(12) United States Patent
Kashima et al.

(10) Patent No.: US 6,255,484 B1
(45) Date of Patent: Jul. 3, 2001

(54) CYANURATE COMPOUND HAVING THREE OXETANE RING GROUPS AND ORGANIC HARDENING COMPOSITIONS CONTAINING SAME

(75) Inventors: Mikito Kashima; Yumiki Noda; Harutoshi Hoshino; Toshikazu Machida, all of Ichihara (JP)

(73) Assignee: Ube Industries, Ltd., Yamaguchi (JP)

( * ) Notice: Subject to any disclaimer, the term of this patent is extended or adjusted under 35 U.S.C. 154(b) by 0 days.

(21) Appl. No.: 09/672,153

(22) Filed: Sep. 27, 2000

(30) Foreign Application Priority Data

Sep. 28, 1999 (JP) .................................................. 11-274160

(51) Int. Cl.$^7$ ...................... C07D 251/30; C07D 305/06; C09K 3/00
(52) U.S. Cl. .................... 544/219; 549/510; 252/182.13; 252/405
(58) Field of Search .............................. 544/219; 549/510

(56) References Cited

U.S. PATENT DOCUMENTS

| 5,463,084 | 10/1995 | Crivello et al. ........................ 549/60 |
| 5,750,590 | 5/1998 | Schaefer et al. ...................... 523/115 |

FOREIGN PATENT DOCUMENTS

| 1021858 | * | 1/1958 | (DE) . |
| 1 021 858 | | 7/1958 | (DE) . |
| 6-16804 | | 1/1994 | (JP) . |
| 7-53711 | | 2/1995 | (JP) . |
| 8-245783 | | 9/1996 | (JP) . |
| 9-309950 | | 12/1997 | (JP) . |
| 10-212343 | | 8/1998 | (JP) . |
| 11-116663 | | 4/1999 | (JP) . |
| 11-140171 | | 5/1999 | (JP) . |

OTHER PUBLICATIONS

J.M.S. –Pure Appl. Chem. A30(2&3)), pp. 189–206 (1993).
Patent Abstract of Japan 07053711.
Patent Abstract of Japan 09309950.
Patent Abstract of Japan 10212343.
Patent Abstract of Japan 11116663.
Patent Abstract of Japan 11140171.

* cited by examiner

*Primary Examiner*—Mukund J. Shah
*Assistant Examiner*—Venkataraman Balasubramanian
(74) *Attorney, Agent, or Firm*—Burgess, Ryan & Wayne; Milton J. Wayne; William R. Moran

(57) ABSTRACT

A cyanurate compound having three oxetane ring groups and represented by the general formula (1):

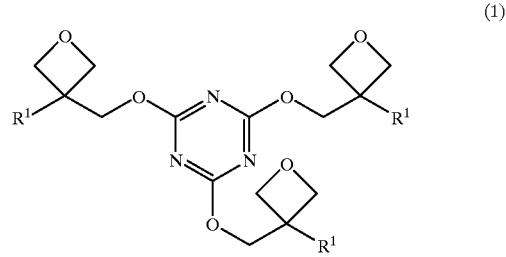

(1)

wherein $R^1$ represents a member selected from the group consisting of a hydrogen atom and alkyl groups having 1 to 6 carbon atoms, is useful as a photosetting monomer or thermosetting monomer, and thus is used, together with a hardening agent, for example, a polycarboxylic anhydride and a catalyst, for example, an amine, a carboxylic acid metal salt or a protonic acid, to provide an organic hardening composition usable for producing electronic materials, for example, resists.

4 Claims, No Drawings

CYANURATE COMPOUND HAVING THREE OXETANE RING GROUPS AND ORGANIC HARDENING COMPOSITIONS CONTAINING SAME

BACKGROUND OF THE INVENTION

1. Field of the Invention

The present invention relates to a cyanurate compound containing three oxetane ring groups and an organic hardening composition containing the same. More particularly, the present invention relates to a photosetting or thermosetting cyanurate compound containing three oxetane ring groups, and an organic hardening composition containing the same.

The compounds having oxetane ring groups are photosetting or thermosetting monomers. The resins derived from the oxetane ring group-containing compounds generally exhibit excellent heat resistance, mechanical properties and adhesiveness. Thus, the oxetane ring group-containing compounds are useful as materials for shaped articles such as, for example, parts of electric devices, heat-resistant resists, coating materials and adhesives and as cross-linking agents and modifying agents for powder coating materials.

2. Description of the Related Art

Compounds containing oxetane ring groups (which will be referred to as oxetane compounds hereinafter) currently draw attention as cationically polymerizable monomers. Thus, various types of mono-functional or poly-functional oxetane compounds, for example, shown below have been reported.

(a) Pure Appl. Chem., A30 (2 &3), pp.189–206 (1993) discloses methods of synthesizing various oxetane compounds.

(b) DE Patent No. 1,021,858 discloses an oxetane compound represented by the formula (a):

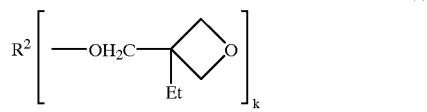

wherein $R^2$ represents an alkyl, aryl, aralkyl, cycloalkyl or di- or valent aromatic group; Et represents an ethyl group; and k represents an integer of 1 or 2.

(c) Japanese Unexamined Patent Publication No. 6-1.6804 discloses an oxetane compound of the formula (b):

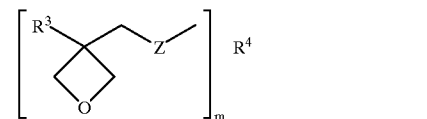

wherein $R^3$ represents a hydrogen or fluorine atom, or an alkyl group with 1 to 6 carbon atoms, a fluoroalkyl group with 1 to 6 carbon atoms, an alkyl group, an aryl group, or a thienyl group; $R^4$ represents a multi-valent organic group selected from straight or branched chain poly (alkyleneoxy) groups, xylylene group, siloxane bond groups and ester bond groups; Z represents a oxygen or sulfur atom; and m represents an integer of 2 to 4.

(d) Japanese Unexamined Patent Publication No. 8-245,783 discloses a plurality of oxetane compounds, for example, di-functional oxetane compounds having a 2,2'-bitolylenediyl skeleton.

(e) Japanese Unexamined Patent Publication No. 9-309,950 and No. 10-212,343 disclose oxetane compounds of the formula (c):

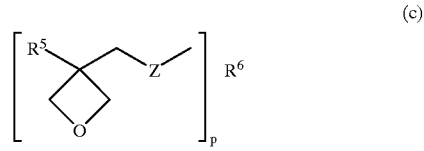

wherein p represents an integer of 1 to 4; $R^5$ represents a hydrogen or fluorine atom or an alkyl group with 1 to 6 carbon atoms, an alkyl group, an aralkyl group, an aryl group, a furyl group or a thienyl group; $R^6$ represents a hydrogen-atom when p is 1, or an organic group having a valence corresponding to the integer represented by p when p is 1 to 6; Z represents an oxygen or sulfur atom.

When the oxetane compounds are utilized as components of thermosetting resin compositions, the resultant thermoset resins are unsatisfactory in the heat resistance thereof. Particularly, in the field of the electronic materials, for example, resists, there is a strong demand for new type of oxetane compounds capable of forming thermosetting resin materials having excellent heat resistance.

In the prior art, no cyanuric acid derivatives having the oxetane ring groups and no synthetic methods for preparing the compounds were known.

Also, no organic hardening composition containing, as a hardening component, a cyanurate compound having the oxetane ring group was known before the present invention.

SUMMARY OF THE INVENTION

An object of the present invention is to provide a cyanurate compound having three oxetane ring groups which can be produced from available starting materials, and an organic hardening composition comprising, as a hardening component, the above-mentioned cyanurate compound.

Another object of the present invention is to provide a cyanurate compound having three oxetane ring groups which can be converted to a hardened product having excellent heat resistance and useful as a material, for example, a resist, for the electronic material field, and an organic hardening composition comprising, as a hardening component, the above-mentioned cyanurate compound.

The above-mentioned objects can be attained by the cyanurate compound of the present invention, having three oxetane ring groups and represented by the general formula (1):

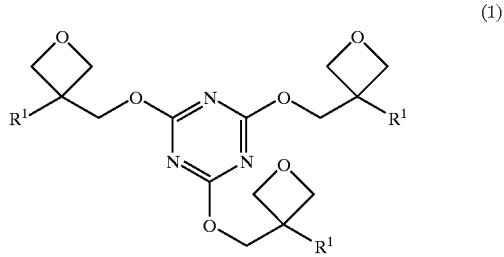

wherein $R^1$ represents a member selected from the group consisting of a hydrogen atom and alkyl groups having 1 to 6 carbon atoms.

In the oxetane ring group-containing cyanurate compound of the present invention, in the formula (1), $R^1$ preferably represents a member selected from the group consisting of methyl and ethyl group.

The oxetane ring group-containing cyanurate compound, of the present invention, may comprise a reaction product of a 3-hydroxymethyloxetane compound, represented by the formula (2):

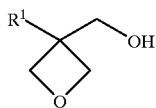

(2)

wherein $R^1$ is as defined above, with cyanuric chloride of the formula (3):

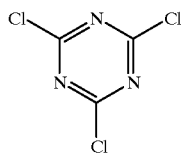

(3)

in the presence of a basic substance.

The oxetane ring group-containing cyanurate compound of the present invention may comprising a reaction product of an alkali metal alcoholate of a 3-hydroxymethyloxetane compound of the formula (2):

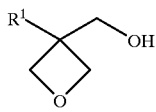

(2)

wherein $R^1$ is as defined above, with cyanuric chloride of the formula (3):

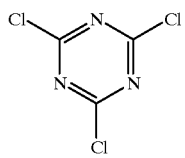

(3)

Also, the above-mentioned objects can be attained by the organic hardening composition of the present invention comprising, as a hardening component (A), at least one cyanurate compound having three oxetane ring groups, as defined above.

In the organic hardening composition of the present invention, the component (A) consisting of the oxetane ring group-containing cyanurate compound may be mixed with a hardening agent component (B) consisting of at least one polycarboxylic anhydride and a catalyst component (C).

In the organic hardening composition of the present invention, the polycarboxylic anhydride for the hardening agent component (B) may be selected from the group consisting of cycloaliphatic polycarboxylic anhydrides, aromatic polycarboxylic anhydrides and aliphatic polycarboxylic anhydrides.

In the organic hardening composition of the present invention, the hardening agent component (B) may be present in an equivalent amount of 0.7 to 1.0 times the equivalent amount of the oxetane ring in the oxetane ring group-containing cyanurate compound in the hardening component (A).

In the organic hardening composition of the present invention, the catalyst component (C) may comprises at least one member selected from amine compounds, metal carboxylates, protonic acids and tetra-alkoxytitaniums.

In the organic hardening composition of the present invention, the catalyst component (C) may be present in an equivalent amount corresponding to 1.0 to 7.0% of the equivalent amount of the oxetane ring groups of the oxetane ring group-containing cyanurate compound contained in the hardening component (A).

The organic hardening composition of the present invention optionally comprises at least one additional component (D) selected from the group consisting of hydroxyl group-containing compounds and epoxy compounds.

In the organic hardening composition of the present invention, the hydroxyl group-containing compounds for the additional component (D) may be selected from the group consisting of water, aliphatic monohydric alcohols having 1 to 12 carbon atoms and aliphatic polyhydric alcohols having 2 to 10 carbon atoms.

The organic hardening composition of the present invention optionally comprises a further additional component (E) comprising at least one epoxy compound.

In the organic hardening composition of the present invention, the epoxy compounds for the further additional component (E) may be selected from the group consisting of aromatic epoxy compounds, and cycloaliphatic epoxy compounds.

The organic hardening composition as mentioned above can be hardened to provide a hardened product.

DESCRIPTION OF THE PREFERRED EMBODIMENTS

The cyanurate compound of the general formula (1) of the present invention has three oxetane ring groups, non-substituted or substituted at a 3-position thereof with a substituent selected from $C_1$–$C_6$ alkyl groups, and each attached to 2,4 or 6-position of a 1,3,5-triazine ring structure, through a —$OCH_2$— group.

In the formula (1), $R^1$ represents a hydrogen atom or an alkyl group having 1 to 6 carbon atoms, preferably a methyl, ethyl, n-propyl or n-butyl group, more preferably a methyl or ethyl group.

The oxetane group-containing cyanurate compound of the formula (1) may be produced by a reaction of a 3-hydroxymethyloxetane compound of the formula (2) (which will be referred to as an oxetane alcohol compound) with a cyanuric trichloride (2,4,6-trichloro-1,3,5-triazine) of the formula (3) in the presence of a basic substance.

In the formula (2), $R^1$ represents a hydrogen atom or an alkyl group having 1 to 6 carbon atoms, preferably a methyl, ethyl, n-propyl or n-butyl group, more preferably a methyl or ethyl group.

Thus, the oxetane alcohol compounds of the formula (2) are preferably 3-methyl-3-hydroxymethyl, oxetane and 3-ethyl-3-hydroxymethyl oxetane.

The oxetane alcohol compound can be easily prepared by, for example, reacting 1,1,1-trimethylolalkane with a dialkyl carbonate to produce a cyclic carbonate and then subjecting the cyclic carbonate to a decarboxylation reaction, in accordance with the method disclosed in J. Am. Chem. Soc. pp 79 (1957). The reaction of the oxetane alcohol compound with the cyanuric trichloride can be effected with a high efficiency in the presence of a basic substance. In this reaction, the oxetane alcohol compound is preferably employed in an amount of 2.5 to 10 moles, more preferably 3 to 5 moles, per mole of the cyanuric trichloride. The basic substance is preferably employed in an amount of 2.5 to 10 moles, more preferably 3 to 5 moles, per mole of the cyanuric trichloride.

The basic substance for the oxetane group-containing cyanurate compound-producing reaction is selected from water-soluble inorganic bases, for example, hydroxides and carbonates of alkali metals and water-soluble organic bases, for example, pyridine and aliphatic tertiary amines. The alkali metal hydroxides include sodium hydroxide and potassium hydroxide and the alkali metal carbonates include sodium carbonate and potassium carbonate. Also, the aliphatic tertiary amines include, for example, triethylamine. Among the above-mentioned bases, the inorganic bases are preferably employed in the state of an aqueous solution thereof for the above-mentioned method.

More preferably, an aqueous solution of an alkali metal hydroxide is employed.

In this case, the inorganic base concentration in the aqueous solution is preferably 10 to 70% by weight, more preferably 30 to 60% by weight.

The above-mentioned reaction is effected by mixing the basic substance into a reaction system comprising the oxetane alcohol compound of the formula (2) and the, cyanuric trichloride of the formula (3). The reaction temperature is preferably 0 to 50° C., more preferably 5 to 30° C. In the mixing procedure, the basic substance is preferably added at a mixing rate in which the reaction system can be maintained in the range of the above-mentioned reaction temperature. There is no specific limitation to the reaction pressure. Thus the reaction may be carried out at the ambient atmospheric pressure, at a reduced pressure or above the ambient atmospheric pressure. A reaction time of 1 to 10 hours is long enough to complete the reaction. Also, the cyanuric trichloride may be placed in one single adding procedure or two or more separate adding procedures into the reaction system. The adding procedure of the cyanuric trichloride is preferably carried out in a manner such that the temperature of the reaction system can be maintained within the above-mentioned reaction temperature range.

The above-mentioned reaction of the oxetane alcohol compound with the cyanuric trichloride may be carried out in no reaction medium. Usually, the reaction is preferably carried out in an appropriate reaction medium. The reaction medium is preferably selected from aromatic hydrocarbons, for example, toluene, xylene, etc.; ethers, for example, tetrahydrofurane, dibutylether, etc.; ketones, for example, acetone, etc.; halogenated hydrocarbons, for example, chloroform, etc.; non-protonic polar compounds, for example, dimethyl-formamide, dimethylsulfoxide, etc. These compound may be employed alone or in a mixture of two or more thereof. The reaction medium is preferably employed in an amount of 300 ml to 10 liters, more preferably 500 ml to 5 liters, per mole of cyanuric trichloride.

Where the reaction of the oxetone alcohol compound with cyanuric trichloride is carried out in the presence of a basic substance consisting of an aqueous inorganic base solution, in a reaction medium consisting of a liquid substance non-compatible with the aqueous inorganic base solution, for example, toluene, a phase transfer catalyst is preferably employed to promote the reaction. The phase transfer catalyst may consist of at least one member selected from quaternary ammonium salts and quaternary phosphonium salts, and is employed in an amount of 0.05 to 0.5 mole per mole of cyanuric trichloride present in the reaction system. The quaternary ammonium salts include tetraalkyl ammonium halides, for example, tetraethyl ammonium bromide; and aralkyltrialkyl ammonium halides, for example, benzyltrimethyl ammonium chlorides, and the quaternary phosphonium salts include tetraaryl phosphonium halides, for example, tetraphenyl phosphonium bromide.

After the reaction of the oxetane alcohol compound with the cyanuric trichloride is completed, the resultant reaction mixture is subjected to extraction with a solvent water-rinsing and drying of the extract and removal of the solvent from the extract, to collect the three oxetane ring group-containing cyanurate compound of the formula (1). Particularly, in the case where a water-soluble solvent, for example, tetrahydrofuran or acetone is employed as a reaction medium, the target compound can be easily collected by only diluting the resultant reaction mixture liquid with water; collecting the resultant precipitated solid by a filtration and washing the collected solid with water.

The collected substance can be identified as a new compound by $^1$H-NMR, $^{13}$C-NMR and/or mass spectra.

The three oxetane ring group-containing cyanurate compound of the formula (1) can be produced by another method in which an oxetane alcohol compound of the formula (2) is converted to a corresponding oxetane alcoholate compound with a base, and the resultant oxetane alcoholate compound reacts with cyanuric trichloride of the formula (3). This method will be referred to as an alcoholate reaction method hereinafter.

In the alcoholate reaction method, an oxetane alcohol compound is reacted with a base in a reaction medium. The reaction temperature is preferably 0 to 50° C. There is no limitation to the reaction pressure. The alcoholate-preparing reaction may be carried out at the ambient atmospheric pressure or at a pressure above or below the ambient atmospheric pressure. There is no specific limitation to the reaction atmosphere.

In the alcoholate-preparing reaction, the base is preferably selected from alkali metals and alkali metal hydrides. As an alkali metal, metallic sodium is preferably used and as a alkali metal hydride, sodium hydride is preferably used. The base is preferably employed in an amount of 1 to 1.5 moles per mole of the oxetane alcohol compound of the formula (2).

The reaction medium of the alcoholate-preparing reaction preferably comprises at least one member selected from aromatic hydrocarbons, for example, toluene, xylene, etc.; ethers, for example, tetrahydrofuran, dibutyl ether, etc.; and non-protonic polar compounds, for example, dimethylformamide, dimethylsuflfoxide, etc. These compounds for the reaction medium may be employed alone or in a mixture of two or more thereof. The reaction medium is preferably present in an amount of 100 ml to 3 liters, more preferably 200 ml to 2 liters, per mole of the oxetane alcohol compound in the reaction system.

The oxetane alcoholate-preparing reaction is followed by a reaction of the oxetane alcoholate compound with the cyanuric trichloride, by adding cyanuric trichloride into the oxetane alcoholate compound-containing reaction medium. In this procedure, cyanuric trichloride may be added in the state of a solution in the reaction medium.

In the alcoholate reaction method, cyanuric trichloride is preferably employed in an amount of 0.1 to 0.4 mole, more preferably 0.2 to 0.33 mole, per mole of the oxetane alcoholate. The reaction temperature is preferably 0 to 50° C., more preferably 5 to 30° C. The cyanuric trichloride is preferably added in a manner such that the temperature of the reaction system is maintained within the above-mentioned reaction temperature range.

There is no specific limitation to the reaction pressure. Thus, the reaction may be effected at the ambient atmospheric pressure or at a pressure above or below the ambient atmospheric pressure. The reaction time is usually 1 to 10 hours.

After the reaction is completed, the target three oxetane ring group-containing cyanurate compound can be refined and collected in the same manner as mentioned above.

In the three oxetane ring group-containing cyanurate compound of the present invention represented by the formula (1), the $R^1$ group is preferably a methyl or ethyl group.

The organic hardening composition of the present invention comprises, as a hardening component (A), at least one cyanurate compound having three oxetane ring groups, as defined by the formula (1).

The oxetane ring group containing cyanurate compound of the formula (1) can be hardened by a cationic polymerization thereof. For example, the oxetane ring group-containing cyanurate compound can be polymerized in a polymerization method similar to that disclosed in Japanese Unexamined Patent Publication No. 7-53711, No. 11-116,663 or No. 11-140,171, for known oxetane compounds other than the compound of formula (1). Thus, the oxetane ring group-containing cyanurate compound of the present invention can be utilized as a photosetting monomer or thermosetting monomer for producing shaped articles, for example, parts of electric devices, or heat-resistant resists or coating materials or adhesive materials, or cross-linking agents or modifying agents for powdered coating materials.

Particularly, when the oxetane ring group-containing cyanurate compound of the present invention is employed as a hardening component, in an organic hardening composition, and is hardened, the resultant hardened product exhibits a high glass transition temperature (Tg). Thus, the composition containing the oxetane ring group-containing cyanurate compound of the present invention can be appropriately utilized for producing electronic materials which are required to exhibit a high heat resistance.

In an embodiment of the organic hardening composition, the oxetane ring group-containing cyanurate compound for a hardening component (A) is employed in a mixture with a hardening agent component (B) consisting of at least one polycarboxylic anhydride and a catalyst component (C). This hardening composition optionally contains hydroxyl group-containing compounds as an additional component (D).

Moreover, this hardening composition optionally comprises at least one epoxy compound as a further additional component (E).

The composition containing the epoxy compound in addition to the hardening component (A), the hardening agent component (B) and the catalyst component (C) is usable to produce a hardened product having a higher Tg than that derived from the composition comprising only the components (E), (B) and (C). The hydroxyl group-containing compound for the additional component (D) contributes to promoting the initiation of the cationic polymerization.

The polycarboxylic anhydride for the hardening agent component (B) is preferably selected from cycloaliphatic polycarboxylic anhydrides, aromatic polycarboxylic anhydrides and aliphatic polycarboxylic anhydrides. Particularly, the cycloaliphatic polycarboxylic anhydrides include EPICURE YH-306 (trademark, made by YUKA SHELL EPOXY), tetrahydrophthalic anhydride and hexahydrophthalic anhydride; the aromatic polycarboxylic anhydrides include phthalic anhydride, trimellitic anhydride, pyromellitic anhydride and biphenyltetracarboxylic anhydride; and the aliphatic polycarboxylic anhydrides includes succinic anhydride and maleic anhydride.

The catalyst component (C) comprises at least one catalytic compound capable of causing the oxetane ring group or the epoxy ring group to be opened and to polymerize. The catalytic compound is preferably selected from amine compounds, for example, benzyldimethylamine, triethylenediamine, and 2-ethyl-4-methylimidazole; metal carboxylates, for example, tin octylate; protonic acids, for example, p-toluenesulfonic acid; and tetraalkoxytitaniums, for example, tetrabutoxytitanium and tetraisopropoxytitanium. The catalyst component (C) may comprise one or two or more catalytic compound selected from the above-mentioned compounds.

The hydroxyl group-containing compound for the additional component (D) is preferably selected from water, aliphatic monohydric alcohols having 1 to 12 carbon atoms, for example, methyl alcohol, ethyl alcohol, propyl alcohol, and butyl alcohol; aliphatic polyhydric alcohols having 2 to 10 carbon atoms, for example, 1,4-butanediol, 1,6-hexanediol, trimethylolethane, trimethylolpropane and pentaerythritol.

When the hardening composition contains the epoxy compound for the further additional component (E), the epoxy compound can be selected from epoxy monomers, oligomers and polymers which are usable as epoxy resins, for example, aromatic epoxy resins including bisphenol A epoxy resins and cresol novolak epoxy resins; cycloaliphatic epoxy resins and aliphatic epoxy resins. Particularly, the bisphenol A epoxy resins include EPICOAT 1002 (trademark, made by YUKA SHELL EPOXY); the cresol novolak epoxy resins include EPICOAT 180S (trademark, made by YUKA SHELL EPOXY); and the cycloaliphatic epoxy resins include CELOXIDE 2021 (trademark, made by DAICEL KAGAKU).

In the organic hardening composition of the present invention which contains no epoxy compound for the further additional component (E), the hardening agent component (B) is preferably contained in an equivalent amount of 0.7 to 1.0 times, more preferably 0.8 to 0.9 times, the equivalent amount of the oxetane ring groups in the oxetane ring group-containing cyanurate compound for the hardening component (A).

Also, the catalyst component (C) is preferably present in an equivalent amount corresponding to 1.0 to 7.0%, more preferably 2.0 to 4.0% of the total equivalent amount of the oxetane ring groups in the component (A) and the epoxy ring groups in the further additional component (E). Further, the hydroxyl group-containing compound for the additional component (D) is preferably present in an amount of 2.0 to 10.0 molar %, more preferably 3.0 to 8.0 molar % per equivalent amount of the oxetane ring groups in the component (A).

When the organic hardening composition contains the epoxy compound as a further additional component (E), there is no limitation to a content ratio of the epoxy compound to the component (A). In this case, preferably, the hardening agent component (B) is present in an equivalent amount of 0.7 to 1.0 times, more preferably 0.8 to 0.9 times the total equivalent amount of the oxetane ring groups contained in the component (A) and the epoxy ring groups contained in the additional component (E), and the catalyst component (C) is present in an equivalent amount corresponding to 1.0 to 7.0%, more preferably 2.0 to 4.0%, of the total equivalent amount of the oxetane ring groups contained in the component (A) and the epoxy ring groups contained in the further additional component (E). Also, in this case, the hydroxyl group-containing compound is preferably present in an equivalent amount corresponding to 2.0 to 10.0%, more preferably 3.0 to 8.0% of the total equivalent amount of the oxetane ring groups in the component (A) and the epoxy ring groups in the additional component (D).

The organic hardening composition of the present invention containing the three oxetane ring group-containing cyanurate compound can be advantageously used to obtain a hardened product having a high glass transition temperature (Tg) and thus exhibiting excellent heat resistance.

EXAMPLES

The present invention will be further illustrated by the following examples.

Example 1

A flask equipped with a dropping funnel and a stirrer and having a capacity of 300 ml was charged with 18.44 g (0.1 mole) of cyanuric trichloride and 100 ml of toluene, and the charged mixture was cooled with ice. The ice-cooled mixture was further mixed with 38.33 g (0.33 mole) of 3-ethyl-3-hydroxymethyl-oxetane and 1.10 g (5 millimole) of benzyltriethyl ammonium chloride. While the resultant mixture was stirred in the flask, a 35 weight % aqueous sodium hydroxide solution in an amount of 40.0 g (NaOH content: 0.35 mole) was dropped into the mixture in the flask over a time of 30 minutes. During the dropping procedure, the reaction temperature of the mixture was maintained in the range of from 10 to 15° C. Then, the resultant reaction liquid was stirred at a temperature of 15° C. for 2 hours.

The resultant reaction liquid was placed in a separating funnel, mixed with 200 ml of ethyl acetate and 100 ml of water, then the mixture was vigorously shaken. A separated organic fraction was collected from the funnel and dried with magnesium sulfate. The magnesium sulfate was removed from the dried organic fraction by filtration. From the organic fraction, the reaction medium was distilled and removed under reduced pressure. A white solid substance was obtained in an amount of 39.5 g.

The white solid substance was subjected to high performance liquid chromatography, CI-MS analysis, $^1$H-NMR analysis and $^{13}$C-NMR analysis. The white solid substance had a degree of purity of 93.8%, and the principal component thereof was identified as a compound of the formula (1) wherein $R^1$ is an ethyl group. The yield of the target compound was 88%.

The analysis results of the white solid substance was as follows.

CI-MS: molecular weight=423

$^1$H-NMR (CDCl$_3$, Me$_4$Si): δ 0.92 (t, J=7.5 Hz 9H) 1.85 (q, J=7.5 Hz, 6H), 4.45 (d, J=6 Hz, 6H) 4.55 (d, J=6 Hz, 6H), 4.60 (s, 6H) $^{13}$C-NMR (CDCl$_3$, Me$_4$Si): δ 8.01, 26.18, 42.65, 70.24, 77.72, 173.07

Example 2

A flask equipped with a dropping funnel and a stirrer and having a capacity of 500 ml was charged with 13.20 g (0.33 mole) of sodium hydride (dispersed in a content of 60% by weight in mineral oil) in a nitrogen gas atmosphere. Then, 30 ml of hexane was charged into the flask and fully dispersed in the sodium hydride dispersion. The resultant mixture was left to stand and a resultant upper clear liquid fraction was collected by pipet. The above-mentioned hexane treatment was repeated twice to remove the mineral oil accompanying the sodium hydride.

Into the flask, 200 ml of tetrahydrofuran was charged, and the resultant mixture in the flask was cooled with ice. Then, 38.33 g (0.33 mole) of 3-ethyl-3-hydroxy-methyloxetane was placed in the dropping funnel and dropped to the mixture in the flask at a dropping rate at which the temperature of the reaction mixture was maintained in the range of from 10 to 15° C. The dropping time was about 40 minutes. After the dropping was completed, the resultant mixture was further stirred at the above-mentioned temperature for 30 minutes.

Into the resultant reaction mixture containing sodium alcholate of 3-ethyl-3-hydroxymethyloxetane, a solution of 18.44 g (0.1 mole) of cyanuric trichloride in 100 ml of tetrahydrofuran was dropped at a dropping rate while the temperature of the reaction mixture is maintained in the range of from 10 to 15° C. The dropping time was about 45 minutes. After the dropping was completed, the resultant mixture was further stirred at a temperature of 15° C. for 2 hours.

The resultant reaction liquid was placed in a separating funnel, and mixed with 500 ml of ethyl acetate and 500 ml of water, and the resultant mixture was vigorously shaken. A resultant separated organic fraction was collected and dried with magnesium sulfate. The magnesium sulfate was removed from the dried organic fraction by filtration. The reaction medium was distilled and removed from the organic fraction under a reduced pressure. A white solid substance was obtained in an amount of 38.00 g.

The white solid substance was analyzed by high performance liquid chromatography. The degree of purity of the principle component in the white solid substance was 96.5%. As the result of the analysis, it was confirmed that the principle component consisted of the same compound as in Example 1. The yield of the target compound was 87%.

Example 3

A solution of 30% by weight of a thermosetting composition containing a three oxetane ring group-containing cyanurate compound, a hardening agent, a catalyst and a hydroxyl compound, and dissolved in dimethyl formamide was prepared.

The three oxetane ring group-containing cyanurate compound was the same as that prepared in Example 1.

The hardening agent consisted of EPICURE YH-306 (trademark, made by YUKA SHELL EPOXY). The catalyst consisted of benzyldimethylamine. The hydroxyl compound consisted of water.

The component compounds were employed in the amounts shown in Table 1.

The resultant composition solution in dimethyl formamide was coated on a surface of a glass plate and the coated solution was heated at a temperature of 160° C. for one hour and then at 200° C. for 30 minutes to harden the solution. The resultant hardened film was subjected to a dynamic viscoelasticity test to determine the glass transition temperature of the film. The film exhibited a glass transition temperature (Tg) of 133° C. The test was carried out by using the following tester under the following conditions.

Tester: Solid viscoelasticity analyzer (model: RSA 11, made by RHEOMETRICS)

Testing mode: Tensile mode Dynamic testing

SWEEP TYPE: Temperature steps 3° C./step Soak time 0.5 minute

Frequency: 10 Hz

Strain: 0.05%

Temperature range: 20 to 280° C.

Atmosphere: In nitrogen gas stream

Comparative Example 1

A thermosetting composition was prepared by the same procedures and from the same components as those in Example 3, except that an epoxy resin available under the trademark of EPICOAT 1002, made by YUKA SHELL EPOXY, and having an epoxy equivalent amount of 600 to 700 g/eq. was further added in the amount shown in Table 1. The composition was hardened and tested in the same manner as in Example 3. The resultant hardened film exhibited a glass transition temperature (Tg) of 105° C.

Comparative Example 2

A thermosetting composition was prepared by the same procedures and from the same components as those in Example 3, except that the oxetane group-containing cyanurate compound was replaced by an epoxy resin available under the trademark of EPICOAT 180S, made by YUKA SHELL EPOXY, and having an epoxy equivalent amount of 205 to 220 g/eq., in the amount shown in Table 1. The composition was hardened and tested in the same manner as in Example 3. The resultant hardened film exhibited a glass transition temperature (Tg) of 108° C.

Example 4

A thermosetting composition was prepared and tested by the same procedures as in Example 3, except that the composition contained the components in the contents shown in Table 1. Namely, the oxetane ring group-containing cyanurate compound, the hardening agent, the catalyst and the hydroxyl compound were the same as those in Example 3, and the epoxy resin was the same as in Comparative Example 1.

The hardened film of the composition exhibited a Tg of 130° C.

Comparative Example 3

A thermosetting composition was prepared by the same procedures and from the same components as those in Example 4, except that the oxetane ring group-containing cyanurate compound was replaced by 1,4-bis[(3-ethyl-3-oxetanyl)methoxymethyl] benzene in the amount shown in Table 1. The composition was tested in the same manner as in Example 4.

The hardened film of the composition exhibited a Tg of 89° C.

Example 5

A thermosetting composition was prepared and tested for the glass transition temperature by the same procedures as in Example 3, except that as a hardening agent, phthalic anhydride was employed in the amount. shown in Table 1.

The hardened film of the composition exhibited a Tg of 180° C.

Comparative Example 4

A thermosetting composition was prepared by the same procedures and from the same components as those in Example 5, except that the oxetane group-containing cyanurate compound was replaced by an epoxy resin available under the trademark of EPICOAT 180S, made by YUKA SHELL EPOXY, and having an epoxy equivalent amount of 205 to 220 g/eq., in the amount shown in Table 1. The composition was hardened and tested in the same manner as in Example 3. The resultant hardened film exhibited a glass transition temperature (Tg) of 134° C.

Comparative Example 5

A thermosetting composition was prepared by the same procedures and from the same components as those in Example 3, except that the oxetane group-containing cyanurate compound was replaced by [(3-ethyl-3-oxetanyl) methyl] terephthalate ester in the amount shown-in Table 1. The composition was hardened and tested in the same manner as in Example 3. The resultant hardened film exhibited a glass transition temperature (Tg) of 125° C.

The compositions and the test results of the thermosetting resinous compositions of Examples 3 to 5 and Comparative Examples 1 to 5 are shown in Table 1.

TABLE 1

| | | Thermosetting composition | | | | | |
|---|---|---|---|---|---|---|---|
| Example No. | | Component (A) (meq) | Epoxy compound (meq) | Component (B) (mmol) | Component (C) (mmol) | OH group-containing compound (mmol) | glass transition temperature (° C.) |
| Example | 3 | CY:10 | — | YH:9 | BDMA:1 | Water:2 | 133 |
| Comparative | 1 | — | Bis:10 | YH:9 | BDMA:1 | Water:2 | 105 |
| Example | 2 | — | Cre:10 | YH:9 | BDMA:1 | Water:2 | 108 |
| Example | 4 | CY:10 | Bis:10 | YH:18 | BDMA:1 | Water:2 | 130 |
| Comparative Example | 3 | XY:10 | Bis:10 | YH:18 | BDMA:1 | Water:2 | 89 |
| Example | 5 | CY:10 | — | PA:9 | BDMA:1 | Water:2 | 180 |
| Comparative | 4 | — | Bis:10 | PA:9 | BDMA:1 | Water:2 | 134 |
| Example | 5 | TA:10 | — | PA:9 | BDMA:1 | Water:2 | 125 |

[Note]
Component (A): Oxetane ring group-containing compound
Component (B): Polycarboxylic anhydride
Component (C): Catalyst
CY: Three oxetane ring group-having cyanurate compound

TABLE 1-continued

<table>
<tr><th rowspan="2">Example No.</th><th colspan="6">Thermosetting composition</th></tr>
<tr><th>Component (A) (meq)</th><th>Epoxy compound (meq)</th><th>Component (B) (mmol)</th><th>Component (C) (mmol)</th><th>OH group-containing compound (mmol)</th><th>glass transition temperature (° C.)</th></tr>
</table>

XY: Oxetane ring group-containing xylene compound
TA: Oxetane ring group-containing terephthalate compound
Bis: EPICOAT 1002 (trademark)
Cre: EPICOAT 180S (trademark)
YH: EPICURE YH-306 (trademark)
PA: Phthalic anhydride
BDMA: Benzyldimethylamine The three oxetane ring group-containing cyanurate compound of the present invention is a new compound and can be produced from easy available starting materials. The oxetane ring group-containing cyanurate compound can be hardened by the cationic polymerization method by which conventional oxetane compound can be polymerized. Thus, the three oxetane ring group-containing cyanurate compound of the present invention is useful as a photosetting monomer or a thermosetting monomer for producing shaped articles, coating materials, electrical insulating materials and photo-forming materials. Also, the three oxetane ring group-containing cyanurate compound can be hardened to produce a hardened product having a high glass-transition temperature (Tg) and exhibiting excellent heat resistance. Thus, the organic hardening composition containing the three oxetane ring group-containing cyanurate compound is useful in electronic materials field as, for example, a resist.

We claim:

1. A cyanurate compound having three oxetane ring groups of the formula:

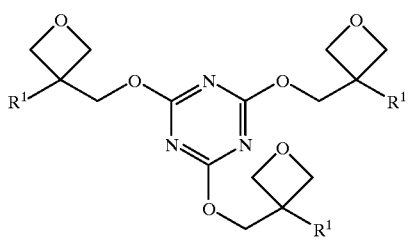
(1)

wherein $R^1$ independently represents a member selected from the group consisting of a hydrogen atom and alkyl groups having 1 to 6 carbon atoms.

2. The oxetane ring group-containing a cyanurate compound as claimed in claim 1, wherein, $R^1$ represents independently, a member selected from the group consisting of a methyl and an ethyl group.

3. The oxetaine ring group-containing a cyanurate compound as claimed in claim 1, comprising a reaction product of a 3-hydroxymethyloxetane compound of the formula:

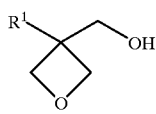
(2)

wherein $R^1$ is as defined above, with cyanuric trichloride of the formula:

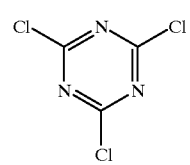
(3)

in the presence of a basic substance.

4. The oxetane ring group-containing a cyanurate compound as claimed in claim 1, comprising a reaction product of an alcoholate of a 3-hydroxymethyloxetane compound of the formula:

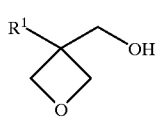
(2)

wherein $R^1$ is as defined above, with cyanuric trichloride of the formula:

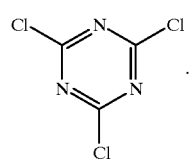
(3)

* * * * *